United States Patent
Kopchick et al.

(10) Patent No.: US 11,975,044 B2
(45) Date of Patent: May 7, 2024

(54) METHODS FOR TREATING CANCERS USING FAT SPECIFIC PROTEIN 27 (FSP27) COMPOSITIONS

(71) Applicant: Ohio University, Athens, OH (US)

(72) Inventors: John J. Kopchick, Athens, OH (US); Vishwajeet Puri, Athens, OH (US); Vishva Sharma, Athens, OH (US); Reetobrata Basu, Athens, OH (US)

(73) Assignee: Ohio University, Athens, OH (US)

( * ) Notice: Subject to any disclaimer, the term of this patent is extended or adjusted under 35 U.S.C. 154(b) by 0 days.

(21) Appl. No.: 17/859,490

(22) Filed: Jul. 7, 2022

(65) Prior Publication Data

US 2023/0059413 A1    Feb. 23, 2023

Related U.S. Application Data

(62) Division of application No. 16/646,009, filed as application No. PCT/US2018/051309 on Sep. 17, 2018, now Pat. No. 11,426,445.

(60) Provisional application No. 62/560,326, filed on Sep. 19, 2017.

(51) Int. Cl.
*A61K 38/17*   (2006.01)
*A61P 31/00*   (2006.01)
*A61P 35/00*   (2006.01)

(52) U.S. Cl.
CPC .......... *A61K 38/1761* (2013.01); *A61P 31/00* (2018.01); *A61P 35/00* (2018.01)

(58) Field of Classification Search
None
See application file for complete search history.

(56) References Cited

U.S. PATENT DOCUMENTS 11,433,117 B2 *   9/2022   Puri .......................... A61P 3/00

FOREIGN PATENT DOCUMENTS

CN            1388132 A   *   1/2003

OTHER PUBLICATIONS

Machine translation of CN 1388132.*
Modi, Shrey et al.; "Control of apoptosis in treatment and biology of pancreatic cancer." J. Cell. Biochem. (2016) 117(2) p. 279-288.*
John, Preethi et al.; "Congestive heart failure secondary to gemcitabine nab-paclitaxel in patients with pancreatic cancer." Anticanc. Res. (2014) 34 p. 7267-7270.*
Huang, Jianfeng et al.; "Tumor induced hyperlipidemia contributes to tumor growth." Cell. Rep. (2016) 15 p. 336-348.*

* cited by examiner

*Primary Examiner* — Fred H Reynolds
(74) *Attorney, Agent, or Firm* — MacMillan, Sobanski & Todd, LLC

(57) ABSTRACT

FSP27 compositions and methods for treating cancers are described.

3 Claims, 13 Drawing Sheets
(3 of 13 Drawing Sheet(s) Filed in Color)
Specification includes a Sequence Listing.

E

FSP27 (120-239)

FSP27 (120-220)

FSP27 (120-210)

FSP27 (140-210)

Functional domains of FSP27

Table 1

| SEQ ID | CF # | Amino acid positions | Peptide length | Peptide Sequence |
|---|---|---|---|---|
| 1 | CF1 | aa 1-60 | 60 | MEYAMKSLSLLYPKSLSRHVSVRTSVVTQQLLSEPSPKAPRARPCRVSTADRSVRKGIMA |
| 2 | CF2 | aa 173-220 | 48 | YDLHCCGAKRIMKEAFRWALFSMQATGHVLLGTSCYLQQLLDATEEGQ |
| 3 | CF3 | aa 40-120 | 81 | PRARPCRVSTADRSVRKGIMAYSLEDLLLKVRDTLMLADKPFFLVLEEDGTTVETEEYFQALAGDTVFMVLQKGQKWQPPS |
| 4 | CF4 | aa 120-140 | 21 | SEQGTRHPLSLSHKPAKKIDV |
| 5 | CF5 | aa 210-220 | 11 | QQLLDATEEGQ |
| 6 | CF6 | aa 210-239 | 29 | QQLLDATEEGQPPKGKASSLIPTCLKILQ |
| 7 | CF7 | aa 120-239 | 120 | SEQGTRHPLSLSHKPAKKIDVARVTFDLYKLNPQDFIGCLNVKATFYDTYSLSYDLHCCGAKRIMKEAFRWALFSMQATGHVLLGTSCYLQQLLDATEEGQPPKGKASSLIPTCLKILQ |
| 8 | CF8 | aa 120-130 | 11 | SEQGTRHPLSL |
| 9 | CF9 | aa 120-210 | 91 | SEQGTRHPLSLSHKPAKKIDVARVTFDLYKLNPQDFIGCLNVKATFYDTYSLSYDLHCCGAKRIMKEAFRWALFSMQATGHVLLGTSCYLQ |
| 10 | CF10 | aa 120-220 | 101 | SEQGTRHPLSLSHKPAKKIDVARVTFDLYKLNPQDFIGCLNVKATFYDTYSLSYDLHCCGAKRIMKEAFRWALFSMQATGHVLLGTSCYLQQLLDATEEGQ |
| 11 | CF11 | aa 140-210 | 71 | VARVTFDLYKLNPQDFIGCLNVKATFYDTYSLSYDLHCCGAKRIMKEAFRWALFSMQATGHVLLGTSCYLQ |
| 12 | CF12 | Aa 1-238 | 238 | MEYAMKSLSLLYPKSLSRHVSVRTSVVTQQLLSEPSPKAPRARPCRVSTADRSVRKGIMAYSLEDLLLKVRDTLMLADKPFFLVLEEDGTTVETEEYFQALAGDTVFMVLQKGQKWQPPSEQGTRHPLSLSHKPAKKIDVARVTFDLYKLNPQDFIGCLNVKATFYDTYSLSYDLHCCGAKRIMKEAFRWALFSMQATGHVLLGTSCYLQQLLDATEEGQPPKGKASSLIPTCLKILQ |

FIG. 15

METHODS FOR TREATING CANCERS USING FAT SPECIFIC PROTEIN 27 (FSP27) COMPOSITIONS

CROSS-REFERENCE TO RELATED APPLICATIONS

This application is a divisional application of Ser. No. 16/646,009 filed Mar. 10, 2020 now allowed, which is a national stage application filed under 35 U.S.C. § 371 of international application PCT/US2018/051309, filed under the authority of the Patent Cooperation Treaty on Sep. 17, 2018, which claims the priority to United States Provisional Application Ser. No. 62/560,326 filed Sep. 19, 2017, the entire disclosures of which are expressly incorporated herein by reference.

SEQUENCE LISTING

The instant application contains a Sequence Listing which has been submitted electronically in XML format and is hereby incorporated by reference in its entirety.Said XML copy, created on Sep. 26, 2022, is named 63631-US-PC-D_OU-18001-DIV_SL.xml and is 20,056 bytes in size.

BACKGROUND OF THE INVENTION

Human cancers of liver, pancreas, and kidney together account for millions of cancer cases and deaths in United States alone every year. All three cancer types are known to be highly resistant to currently known chemotherapy and targeted therapies. Also, these cancers are highly metastatic, and recurrent in nature with very low five-year survival rates of 3%, 2%, and 8% for liver, pancreas and kidney cancers, respectively.

The lack of therapeutic options and increasing resistance to available drugs, creates a huge challenge in cancer therapy. Additionally, the high doses of chemotherapy required at advanced stage causes significant adverse side-effects, deteriorating the quality of life of the patients.

There is a great need for life-saving treatments for the millions of patients suffering from cancers.

There is no admission that the background art disclosed in this section legally constitutes prior art.

SUMMARY OF THE INVENTION

Fat Specific Protein (FSP27), also known as cell death-inducing DFFA-like effector c (CIDEC in humans and Cidec in mice; also abbreviated Cide-c or Cide-3) is a member of the cell death-inducing DNA fragmentation factor-like effector family—a group of genes that play an important role in apoptosis. FSP27 promotes lipid droplet formation in adipocytes and may mediate adipocyte apoptosis. Its function is regulated by insulin. The invention described herein identifies an additional, novel role of FSP27 as a therapeutic target for treating cancer.

In a first broad aspect, described herein are uses of FSP27 compositions. It is now described herein that the exogenous delivery of FSP27 would be able to rescue FSP27 dysfunction or augment the endogenous function of FSP27.

In another broad aspect, described herein are methods of treatment where administering exogenous recombinant FSP27 (rFSP27) as a therapeutic for the treatment of human cancers including but not limited to liver, pancreas, kidney, melanoma, breast, prostate lung, colon and gastric cancers.

Such uses include, but are not limited to, increasing levels of FSP27 in a subject by administering exogenous recombinant FSP27 (rFSP27).

In certain embodiments, one fragment of FSP27, namely amino acids 120-140, inhibits the growth of several types of human cancers.

Described herein are examples showing the anti-cancer activity of exogenously administered human FSP27 and peptide fragments or analogs in human cancers.

Recombinant FSP27 sensitizes melanoma and liver, pancreatic and kidney cancer cells that can then be killed by a very low dose of prescribed chemotherapeutic agents.

Chemotherapy drugs cause adverse side effects but use of recombinant FS27 in combination with significantly lower doses of the chemotherapeutic agents acts to significantly reduce these side effects.

In another broad aspect, described herein are pharmaceutical compositions comprising one or more FSP27 medicaments. FSP27 medicaments may be administered as a pharmaceutically acceptable salt, or as a pegylated composition, or be modified in a pharmaceutically acceptable manner so as to improve the therapeutic properties. FSP27 medicaments may also be administered optionally together with one or more inert carriers and/or diluents.

The FSP27 medicament is present in an amount sufficient to treat one or more types of cancer.

In another broad aspect, described herein is a method of treating a subject, the method comprising: administering a composition comprising a nucleic acid encoding a FSP27 protein or a fragment thereto a subject; wherein, the FSP27 protein has an amino acid sequence having greater than 85% homology to at least one of the FSP27 sequences shown in FIG. 14; or the FSP27 fragments shown in FIG. 15.

In certain embodiments, the FSP27 protein has an amino acid sequence having greater than about 90% homology to the FSP27 sequences.

In certain embodiments, the FSP27 protein has an amino acid sequence having greater than about 95% homology to the FSP27 sequences.

In certain embodiments, the FSP27 protein has an amino acid sequence having greater than about 99% homology to the FSP27 sequences.

In certain embodiments, the FSP27 protein is naturally occurring.

In certain embodiments, the FSP27 protein is a recombinant protein.

In certain embodiments, the FSP27 protein comprises a core FSP27 domain, such as amino acids comprising: aa120-239 of FSP27; aa120-230 of FSP27; aa120-210; aa120-140; aa120-220; aa140-210; and/or aa173-220 of FSP27.

In certain embodiments, the subject is a human.

In certain embodiments, the subject experiences reduced cancer cell viability.

In certain embodiments, the nucleic acid encoding the FSP27 protein is operably linked to a constitutive transcriptional regulatory sequence containing a variety of control elements such as promoters, enhancers, silencers and the like (hereafter collectively called a promoter), an adipocyte-specific promoter, or an inducible promoter.

In certain embodiments, the composition comprises a plasmid, the plasmid comprising the nucleic acid encoding the FSP27 protein operably linked to a promoter.

In certain embodiments, the composition comprises a viral vector, the viral vector comprising the nucleic acid encoding the FSP27 protein operably linked to a promoter.

Various objects and advantages of this invention will become apparent to those skilled in the art from the following detailed description of the preferred embodiment, when read in light of the accompanying drawings.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

FIG. 1A shows the sigmoid inhibition curve for HepG2-24 hr–IC50=65 nM; and, FIG. 1B shows % inhibition for HepG2-24 hr.

FIG. 2A shows the sigmoid inhibition curve for PANC1-24 hr–IC50=132 nM; and, FIG. 2B shows % inhibition for PANC1-24 hr.

FIG. 3A shows the sigmoid inhibition curve for MCF-7-24 hr–IC50=187 nM; and, FIG. 3B shows % inhibition for MCF7-24 hr.

FIG. 4A shows the sigmoid inhibition curve for 786-0–24 hr— IC50>400 nM; and, FIG. 4B shows % inhibition for 786-O-24 hr.

FIG. 5A shows the sigmoid inhibition curve for SK-MEL-28-24 hr–IC50>400 nM; and, FIG. 5B shows % inhibition for SK-MEL-28-24 hr.

FIG. 7A shows % inhibition for HepG2 following 24 hr exposure; and, FIG. 7B shows % inhibition for HepG2 after additional 24 hours following removal of CIDEC (post CIDEC).

FIG. 8A shows % inhibition for SK-MEL-28 following 24 hr exposure; and, FIG. 8B shows % inhibition for SK-MEL-28 after additional 24 hours following removal of CIDEC (post CIDEC).

FIG. 13 discloses SEQ ID NO: 4.

FIG. 15: Table 1, showing the amino acid sequence detail of the relevant peptides.

DETAILED DESCRIPTION OF THE PREFERRED EMBODIMENT(S)

Figure 1A:
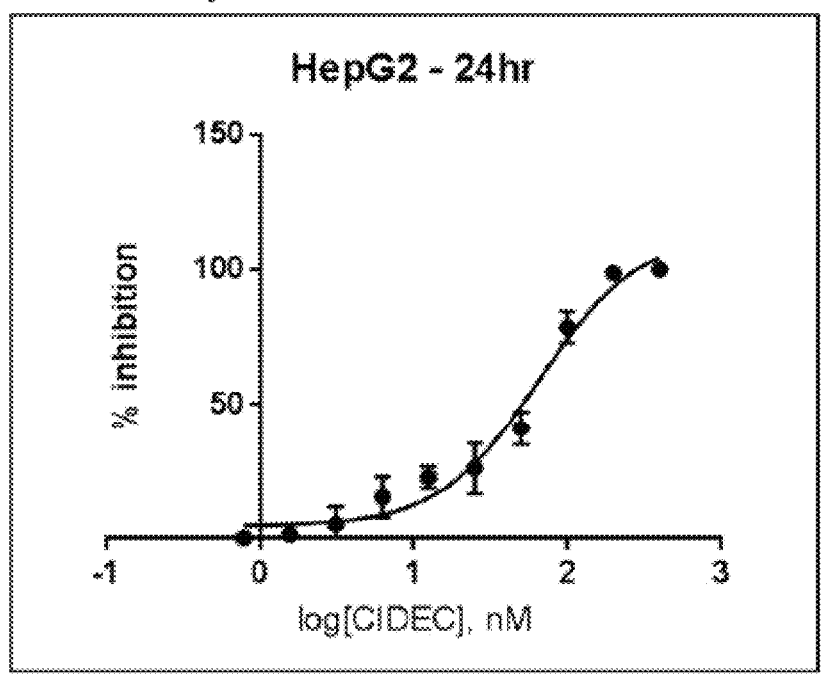
FIGS. 1A-1B: Effect of CIDEC on human liver cancer cell viability; Type: human hepatocellular carcinoma (HCC); Cell: HepG2; Assay: Cell viability assay (Presto-Blue, Invitrogen); Doses (nM): 0-400; Treatment period (hr): 24.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

Definitions

In order to facilitate review of the various embodiments of the disclosure, the following explanations of specific terms are provided:

FSP27: Refers to Fat Specific Protein 27, as well as any other accepted nomenclature for the gene in human or other non-human species, including but not limited to CIDEC, Cidec, Cide-C, and Cide-3.

FSP27 Compositions/Medicaments: Refers to the FSP27 as shown in the schematic representation of FSP27 fragments in FIG. 12A, the amino acids listed in FIG. 14, and the amino acid sequences listed in FIG. 15, including any substitutions, deletions, modifications, or mutations thereof. FSP27 Compositions/Medicaments as contemplated herein may also be prepared as recombinant proteins, including the FSP27 sequences shown in FIG. 14, and in the Table in FIG. 15.

The FSP27 protein is encoded by a nucleic acid sequence or gene. As used herein, a "nucleic acid" or "polynucleotide" includes a nucleic acid, an oligonucleotide, a nucleotide, a polynucleotide, and any fragment or variant thereof. The nucleic acid or polynucleotide may be double-stranded, single-stranded, or triple-stranded DNA or RNA (including cDNA), or a DNA-RNA hybrid of genetic or synthetic origin, wherein the nucleic acid contains any combination of deoxyribonucleotides and ribonucleotides and any combination of bases, including, but not limited to, adenine, thymine, cytosine, guanine, uracil, inosine, and xanthine hypoxanthine. The nucleic acid or polynucleotide may be combined with a carbohydrate, lipid, protein, or other materials. Preferably, the nucleic acid encodes FSP27 protein.

The "complement" of a nucleic acid refers, herein, to a nucleic acid molecule with sufficient homology to recognize, or which will hybridize to another nucleic acid under conditions of high stringency. High-stringency conditions are known in the art (see e.g., Maniatis et al., Molecular Cloning: A Laboratory Manual, 2nd ed. (Cold Spring Harbor: Cold Spring Harbor Laboratory, 1989) and Ausubel et al., eds., Current Protocols in Molecular Biology (New York, N.Y.: John Wiley & Sons, Inc., 2001)). Stringent conditions are sequence-dependent, and may vary depending upon the circumstances. As used herein, the term "cDNA" refers to an isolated DNA polynucleotide or nucleic acid molecule, or any fragment, derivative, or complement thereof. It may be double-stranded, single-stranded, or triple-stranded, it may have originated recombinantly or synthetically, and it may represent coding and/or noncoding 5' and/or 3' sequences.

In addition, "complementary" means not only those that are completely complementary to a region of at least 15 continuous nucleotides, but also those that have a nucleotide sequence homology of at least 40% in certain instances, 50% in certain instances, 60% in certain instances, 70% in certain instances, at least 80%, 90%, and 95% or higher. The degree of homology between nucleotide sequences can be determined by various methods, including an algorithm, BLAST, etc.

As used herein, nucleic acids and/or nucleic acid sequences are "homologous" when they are derived, naturally or artificially, from a common ancestral nucleic acid or nucleic acid sequence. Homology is generally inferred from sequence identity between two or more nucleic acids or proteins (or sequences thereof). The precise percentage of identity between sequences that is useful in establishing homology varies with the nucleic acid and protein at issue, but as little as 25% sequence identity is routinely used to establish homology. Higher levels of sequence identity, e.g., 30%, 40%, 50%, 60%, 70%, 80%, 90%, 95%, 96%, 97%, 98%, or 99% or more can also be used to establish homology. Methods for determining sequence similarity percentages (e.g., BLASTN using default parameters) are generally available. Software for performing BLAST analyses is publicly available through the National Center for Biotechnology Information.

The nucleic acid agent, for example, may be a plasmid. Such a plasmid may comprise a nucleic acid sequence encoding FSP27, variants or isoforms thereof, although it is to be understood that other types of nucleic acid agents, such as recombinant viral vectors, may also be used for the purposes of the present invention. In one embodiment of the present invention, the nucleic acid (e.g., plasmid) encodes at least one FSP27 variant or isoform.

The term "plasmid", as used herein, refers generally to circular double-stranded DNA, which is not bound to a chromosome. The DNA, for example, may be a chromosomal or episomal-derived plasmid. The plasmid of the present invention may optionally contain an initiator or promoter of transcription, terminator of transcription, translational control sequences, and/or a discrete series of restriction-endonuclease recognition sites, located between the promoter and the terminator. In the plasmid, a polynucleotide insert of interest (e.g., one encoding a FSP27-associated protein) should be operatively linked to an appropriate promoter. The promoter may be its native promoter or a host-derived promoter. The promoter may also be a tissue-specific promoter, such as an adipocyte-specific promoter or other tissue-specific promoter. The promoter may further be a regulatable promoter, which may be turned off when the expression of the gene is no longer desired. Non-limiting examples of promoters for use in the present invention include the actin promoter and viral promoters. Other suitable promoters will be known to the skilled artisan.

Therapeutic: A generic term that includes both diagnosis and treatment. It will be appreciated that in these methods the "therapy" may be any therapy for treating a disease including, but not limited to, pharmaceutical compositions, gene therapy and biologic therapy such as the administering of antibodies and chemokines. Thus, the methods described herein may be used to evaluate a patient or subject before, during and after therapy, for example, to evaluate the reduction in disease state.

Adjunctive therapy: A treatment used in combination with a primary treatment to improve the effects of the primary treatment.

Clinical outcome: Refers to the health status of a patient following treatment for a disease or disorder or in the absence of treatment. Clinical outcomes include, but are not limited to, an increase in the length of time until death, a decrease in the length of time until death, an increase in the chance of survival, an increase in the risk of death, survival, disease-free survival, chronic disease, metastasis, advanced or aggressive disease, disease recurrence, death, and favorable or poor response to therapy.

Decrease in survival: As used herein, "decrease in survival" refers to a decrease in the length of time before death of a patient, or an increase in the risk of death for the patient.

Patient: As used herein, the term "patient" includes human and non-human animals. The preferred patient for treatment is a human. "Patient," "individual" and "subject" are used interchangeably herein.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Poor prognosis: Generally refers to a decrease in survival, or in other words, an increase in risk of death or a decrease in the time until death. Poor prognosis can also refer to an increase in severity of the disease, such as an increase in spread (metastasis) of the cancer to other tissues and/or organs.

Screening: As used herein, "screening" refers to the process used to evaluate and identify candidate agents that affect such disease.

Comprising, comprises and comprised of: As used herein are synonymous with "including", "includes" or "containing", "contains", and are inclusive or open-ended and do not exclude additional, non-recited members, elements or method steps. The terms "comprising", "comprises" and "comprised of" also include the term "consisting of".

About: As used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

And/or: When used in a list of two or more items, means that any one of the listed items can be employed by itself or any combination of two or more of the listed items can be employed. For example, if a list is described as comprising group A, B, and/or C, the list can comprise A alone; B alone; C alone; A and B in combination; A and C in combination; B and C in combination; or A, B, and C in combination.

EXAMPLES

Certain embodiments of the present invention are defined in the Examples herein. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Cell Culture and Treatments

Human cancer cell lines (part of NCI-60 panel of human cancer cells)—SK-MEL-5 (melanoma), SK-MEL-28 (melanoma), MCF-7 (breast cancer), 786-0 (renal cancer), A498 (renal cancer), Hep-G2 (liver cancer), SK-HEP-1 (liver cancer), PANC-1 (pancreatic cancer), and normal human skin fibroblast cells MALME-3 cells were obtained from American Type Culture Collection (ATCC; Manassas, VA). The cells were grown and maintained in corresponding complete growth medium—PANC-1 in DMEM medium (ATCC), 786-0 in RPMI-1640 medium, remaining cell lines in EMEM media (ATCC), and MALME-3 in McCoy's medium (ATCC)—as indicated by ATCC protocols. Complete growth media was supplemented with 10% fetal bovine serum (FBS; ATCC) and 1× antibiotic-antimycotic (Thermo Fisher Scientific, Waltham, MA). MALME-3 cells were grown in McCoy's medium (ATCC) supplemented with 15% FBS and 1× antibiotic-antimycotic. Cells were grown at 37C/5% $CO_2$ in a humidified incubator. Media was replaced every third day.

Recombinant hGH was purchased from Antibodies Online (Atlanta, GA), GH antagonist (GHA; Somavert) was obtained from Pfizer (New York City, NY), full length CIDEC was purchased from Abcam (Cambridge, UK) and CIDEC fragment peptides were synthesized at Genscript (Piscataway, NJ). No hGH or GHA was present in the media or added externally unless specifically mentioned. For hGH treatment, 16 hr. after cell seeding (or 24 hr. post-transfection), any GH or GHA or CIDEC or peptides were added at specific concentrations. Cells were subsequently incubated for 48 hr. before subsequent analyses.

Cell Viability Assay

A resazurin based absorption assay was performed measuring cell proliferation, as a measure of inhibition of cell growth/viability. There are several commonly practiced assays using tetrazolium (MTT, MTS, XTT), or resazurin which give a quantitative reflection of cell viability. Although ATP detection assay is the most sensitive of the available options, resazurin-based assay is considered adequate and is routinely used to measure compound EC50s or cell viability following cytotoxic treatments. A stock solution of 1% (w/v) resazurin (Sigma-Aldrich #R7017) in 1×PBS was made and filter-sterilized. The final concentration of resazurin in the assay was 0.004%. Proliferating cells can be quantified by spectrophotometric measurement of a bright pink fluorescent product called resorufin (stable for >4 hr) formed when mildly fluorescent blue resazurin enters a reducing intracellular environment characteristic of proliferating cells. Cells were seeded at 10,000 cells/cm$^2$ into 96-well plates and transfected as described above. The resazurin assay was performed following the respective treatment periods and resorufin absorbance was measured at 570 nm (reference wavelength=600 nm) using Spectramax250 (Molecular Devices, Sunnyvale, CA) and Softmax-Pro software. In all cases, cells were incubated at 37C/5% $CO_2$ for 1 hr following resazurin addition. The resazurin assay for cell proliferation was used to measure EC-50 of relevant drugs and Graph Pad Prism was used to calculate EC-50 shifts (EC50 shift=EC50 of treated cell line/EC50 of parental cell line.

A 1% (w/v) resazurin (Sigma-Aldrich) solution in 1×PBS was made and filter-sterilized. The final concentration of resazurin in the assay was 0.004%. Inside the proliferating cells mildly fluorescent blue resazurin is reduced to a bright pink fluorescent product called resorufin (stable for 4 hr), which is a quantitative measure of the percentage of proliferating cells. In all cases, cells were incubated at 37C/5% $CO_2$ for 45-60 minutes for adequate sensitivity of detection. Briefly, cells were seeded at 10,000 cells/cm$^2$ into 96-well plates and transfected as described above. The resazurin assay was performed 60 hr after transfection (unless specified otherwise) and resorufin absorbance was measured at 570 nm (reference wavelength=600 nm) using Spectramax250 (Molecular Devices) and SoftmaxPro v4.7.1 software.

Statistical Analyses

Parametric and non-parametric statistical analyses were done using R software (ver3.0.2). For resazurin based assays a paired students T-test and ANOVA was performed (using GraphPad Prism software) to compare for significance ($p<0.05$ is considered significant).

Example 1—Anti-cancer Effect of Exogenously Added CIDEC

To confirm if human full-length CIDEC protein had a dose dependent effect in cell viability inhibition of different classes of cancer cells, a 10-dose treatment was used for 24 hr (or 48 hr) with a maximum concentration of 400 nM CIDEC. Dose response analysis of cancers of breast, liver, pancreas, renal and melanoma, and normal human cells against 0-400 nM of CIDEC indicate a variable effect of CIDEC in different cancer types.

Figure 1B:
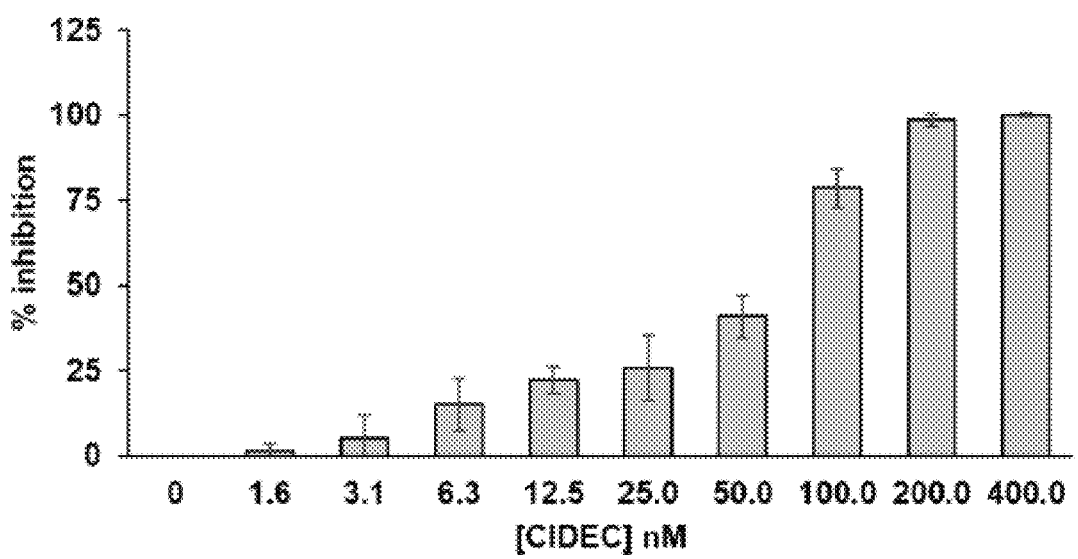

FIGS. 1A-1B show that human liver cancer (HepG2-hepatocellular carcinoma or HCC) cells were found to be significantly responsive to the effects of CIDEC. HepG2 cells had an EC50 (dose that causes 50% decrease of cell viability)=65 nM.

Figure 2A:
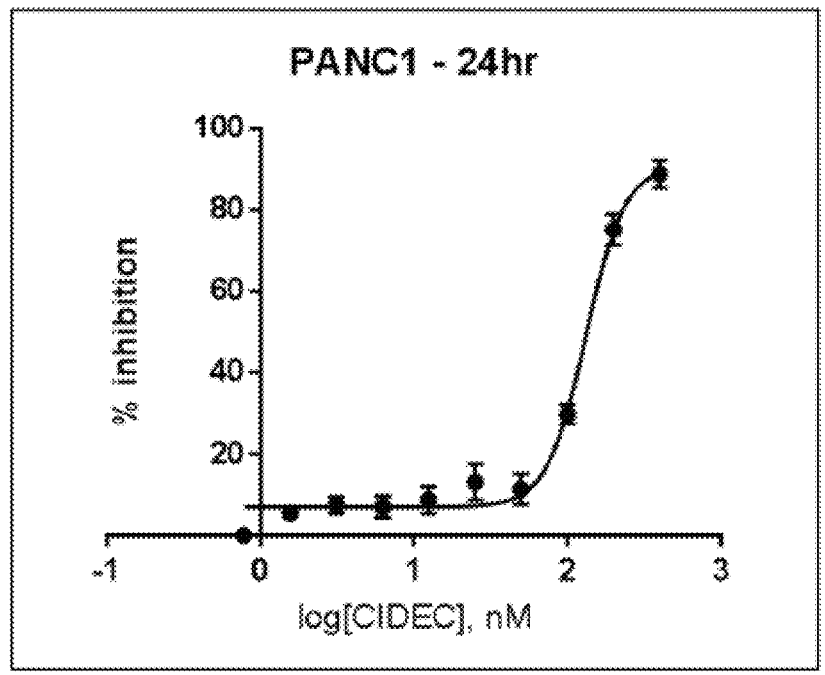
FIGS. 2A-2B: Effect of CIDEC on human pancreatic cancer cell viability; Type: human pancreatic ductal adenocarcinoma (PDAC); Cell: PANC-1; Assay: Cell viability assay (Presto-Blue, Invitrogen); Doses (nM): 0-400;Treatment period (hr): 24.
Figure 2B:
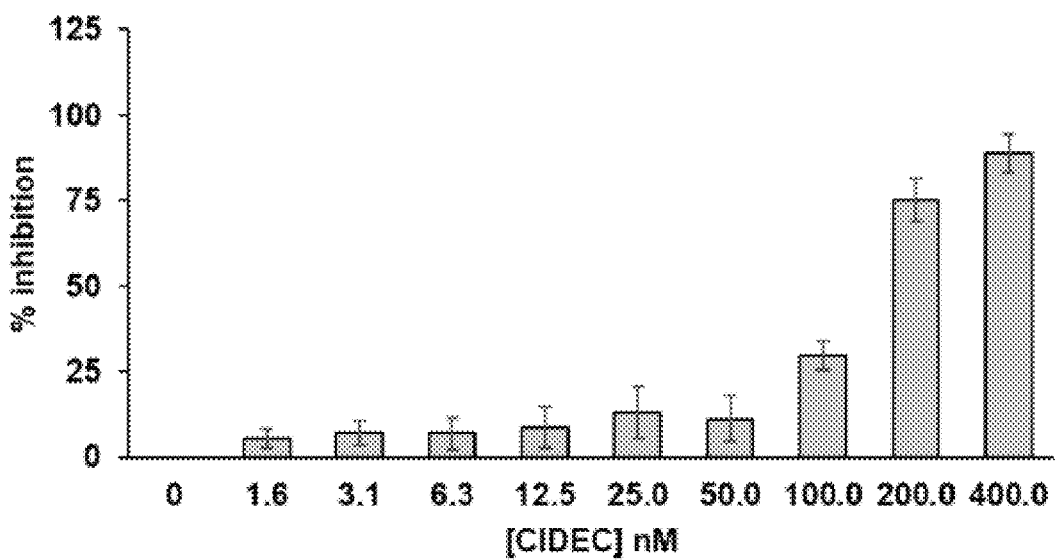

FIGS. 2A-2B show that human pancreatic cancer (PANC-1-pancreatic ductal adenocarcinoma or PDAC) cells were found to be sensitive to the effects of CIDEC. PANC1 cells had an EC50=132 nM.

Figure 3A:
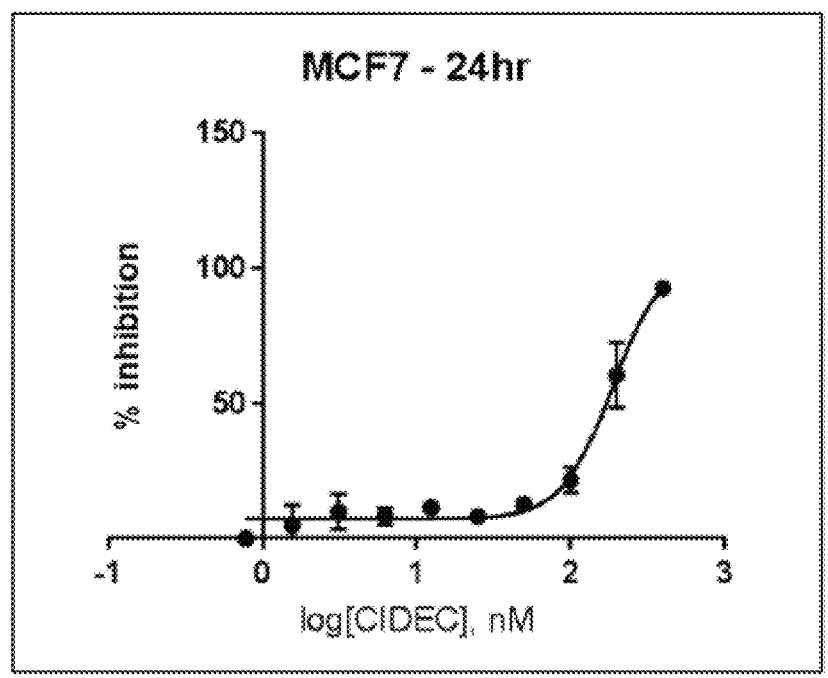
FIGS. 3A-3B: Effect of CIDEC on human breast cancer cell viability; Type: human breast cancer; Cell: MCF-7; Assay: Cell viability assay (Presto-Blue, Invitrogen); Doses (nM): 0-400; Treatment period (hr): 24.
Figure 3B:
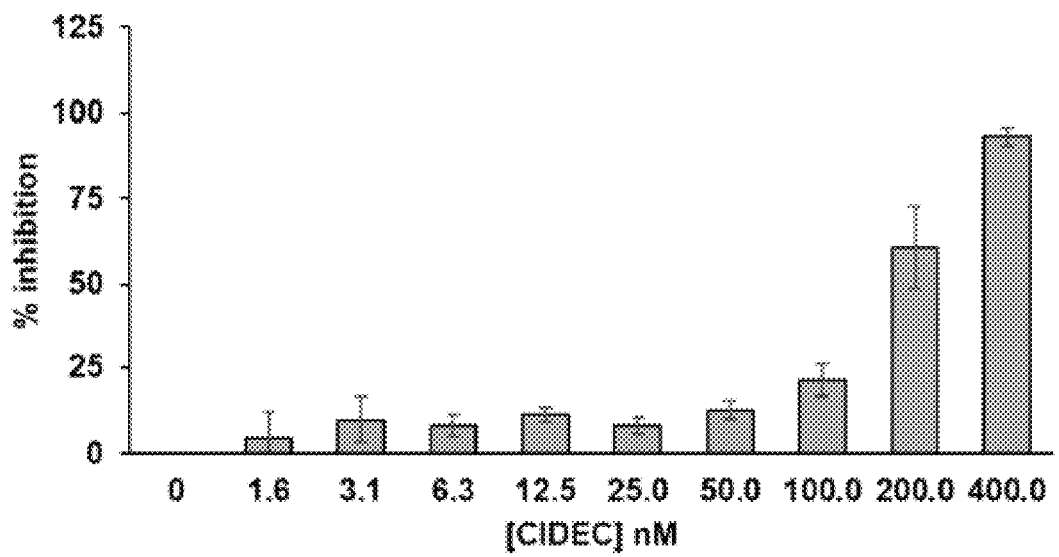

FIGS. 3A-3B show that human breast cancer (BC) cells were also found to be responsive to the effects of CIDEC. MCF-7 cells had an EC50=187 nM.

Figure 4A:
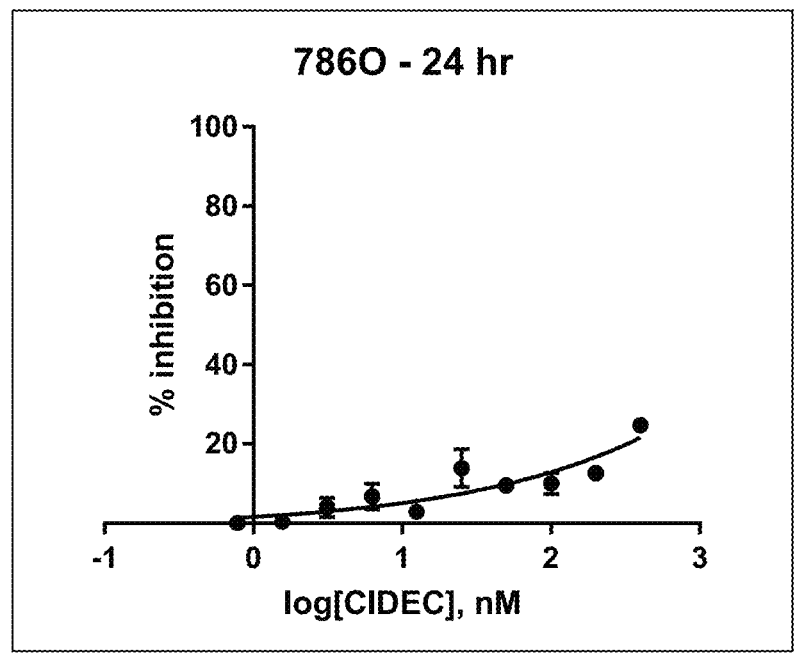
FIGS. 4A-4B: Effect of CIDEC on human renal cancer cell viability; Type: human clear cell renal cell carcinoma (ccRCC); Cell:786-O; Assay: Cell viability assay (Presto-Blue, Invitrogen); Doses (nM): 0-400; Treatment period (hr): 24.
Figure 4B:
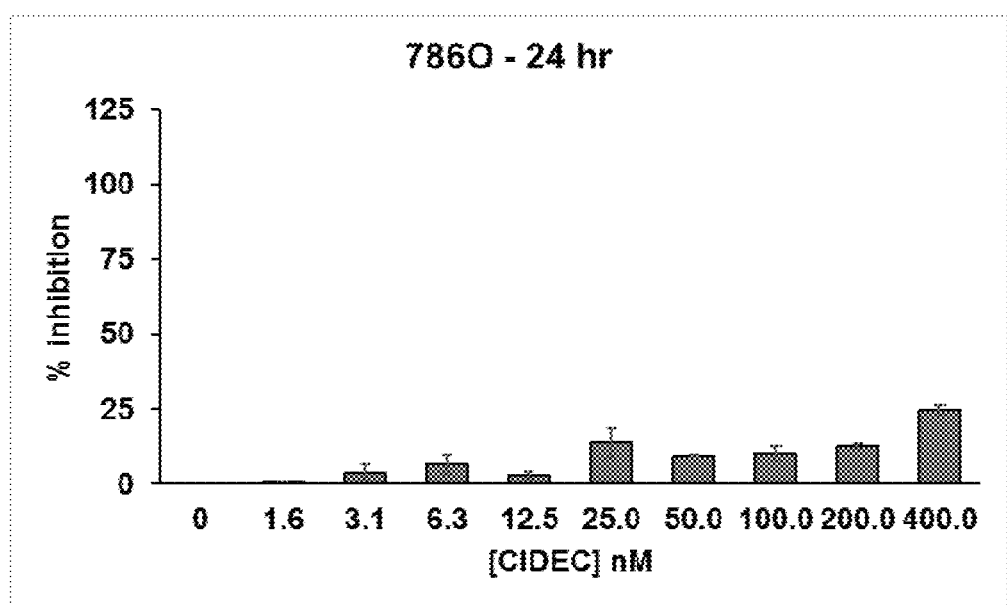

FIGS. 4A-4B show that human renal cancer cells (786-0) were found to be not responsive to the effects of CIDEC up to a dose of 400 nM. 786-0 cells had an EC50>400 nM.

Figure 5A:
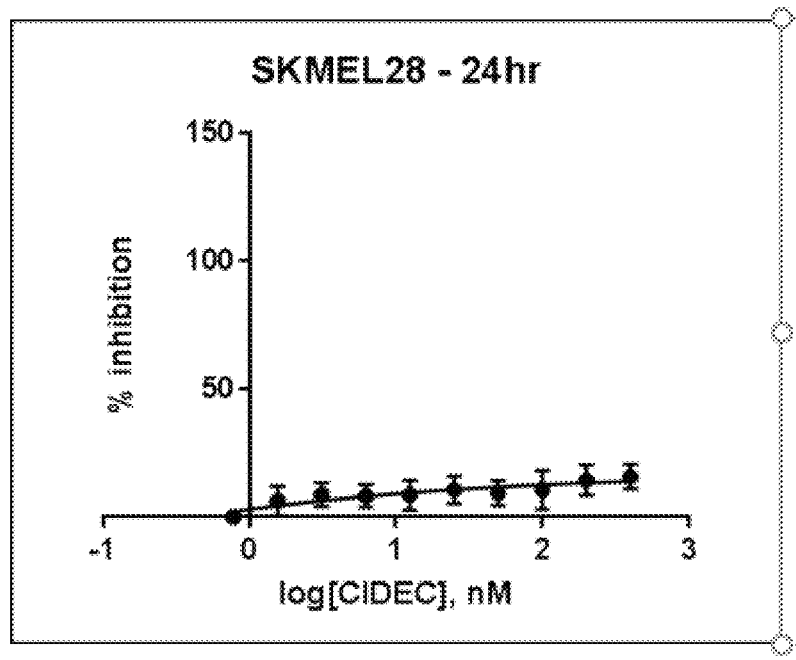
FIGS. 5A-5B: Effect of CIDEC on human melanoma cancer cell viability; Cell: human melanoma cancer (SK-MEL-28) cells; Assay: Cell viability assay (Presto-Blue, Invitrogen); Doses (nM): 0-400 nM; Treatment period (hr): 24.
Figure 5B:
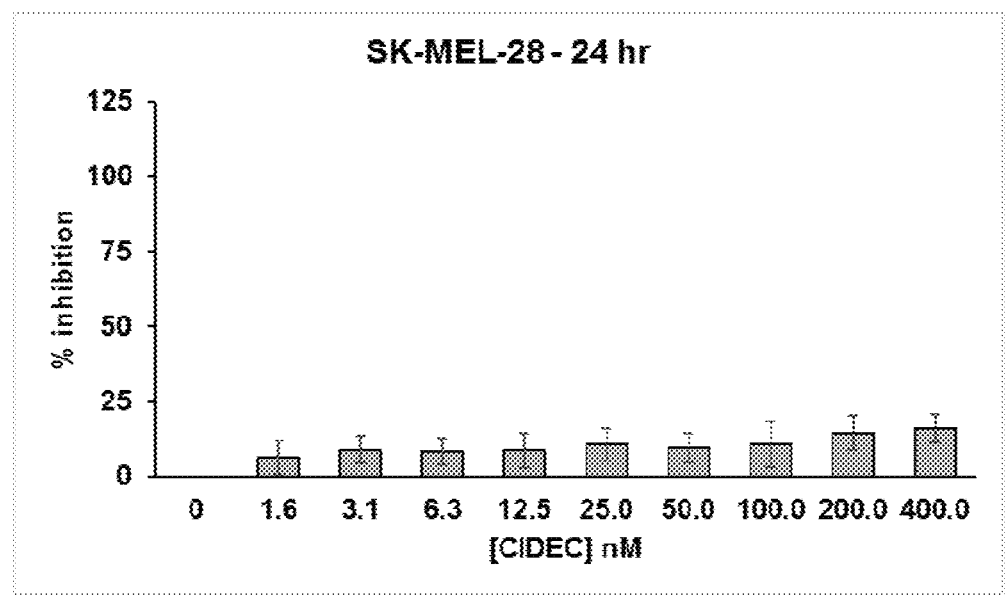

FIGS. 5A-5B shows that human melanoma cells (SK-MEL-28) were found to be not responsive to the effects of CIDEC up to a dose of 400 nM. SK-MEL-28 cells had an EC50>400 nM (FIG. 5).

Figure 6:
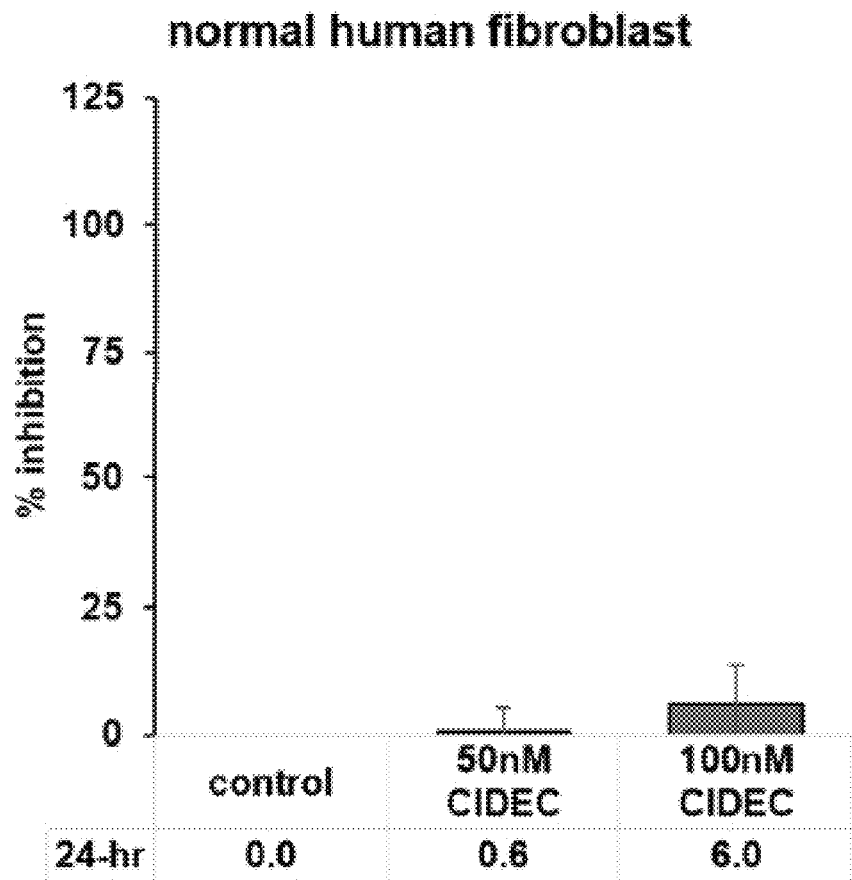
FIG. 6: Effect of CIDEC on human normal fibroblast cells; Cell: human normal fibroblast cells; Assay: Cell viability assay (Presto-Blue, Invitrogen); Doses (nM): 0, 50, 100 nM; Treatment period (hr): 24.

FIG. 6 shows that human normal fibroblast cells showed no significant decrease in cell viability on exposure to up to 100 nM CIDEC.

Example 2—Synthetic Lethality

To confirm if human full-length CIDEC protein had synthetic lethality or a syngenic effect in inhibiting cancer cell viability, when administered with established or prescribed anti-cancer drugs, we treated human melanoma, liver or renal cancer cells with 50 nM CIDEC and different types of anti-cancer drugs for 48 hr. CIDEC did not improve drug effects in case of human melanoma, but showed significant increase in efficacy of sorafenib-tosylate against liver cancer.

Figure 7A:
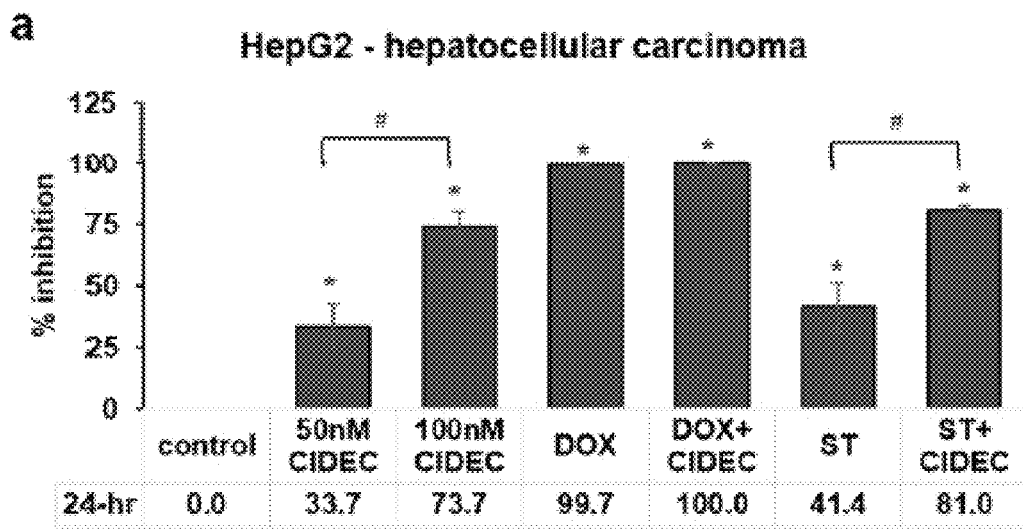
FIGS. 7A-7B: Effect of CIDEC and anti-cancer drugs on human liver cancer cell viability; Type: human hepatocellular carcinoma (HCC); Cell: HepG2; Assay: Cell viability assay (Presto-Blue, Invitrogen); Doses (nM): 0, 50, 100 nM; Treatment period (hr): 24, and +24 after removing CIDEC (post CIDEC); Drugs: Doxorubicin (DOX) @ 300 nm; Sorafenib tosylate (ST) @ 1000 nm.
Figure 7B:
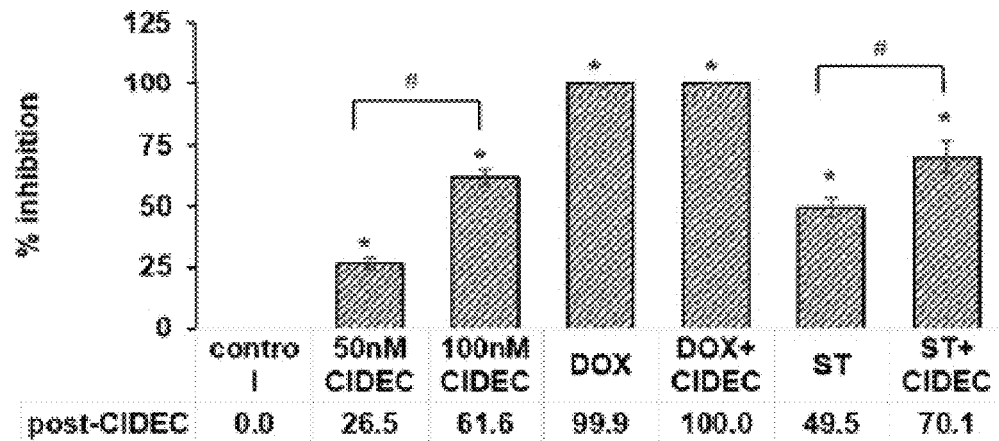

FIGS. 7A-7B show co-administration and 24 hr treatment with full-length CIDEC (fl-CIDEC) caused a significant (2-fold) decrease in cell viability of liver cancer cells treated with sorafenib-tosylate. A similar effect was not seen for doxorubicin, because of supra-EC50 level of doxorubicin (300 nM) used for HepG2 cells (doxorubicin EC50 for HepG2=190 nM), which killed>90% cells even in absence of CIDEC.

Figure 8A:
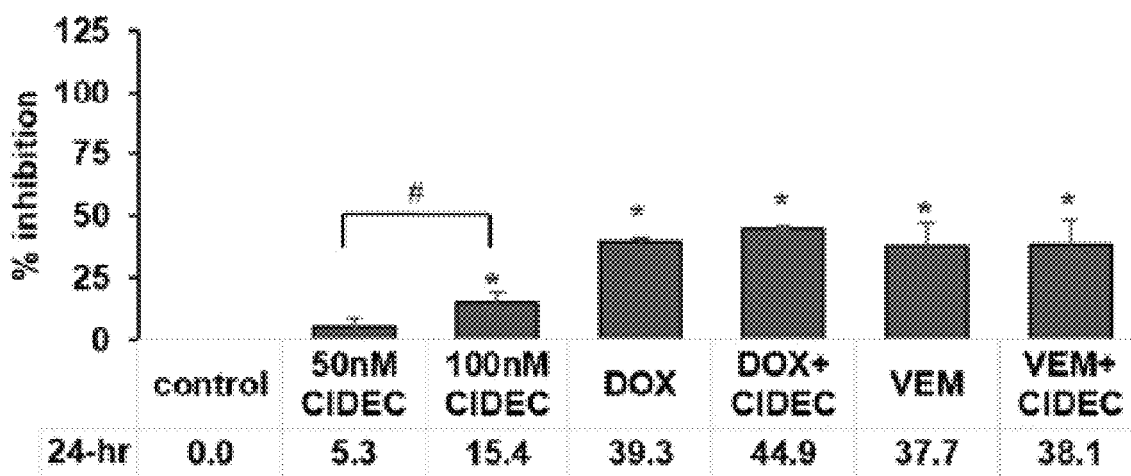
FIGS. 8A-8B: Effect of CIDEC and anti-cancer drugs on human melanoma cell viability; Type: human melanoma; Cell: SK-MEL-28; Assay: Cell viability assay (Presto-Blue, Invitrogen); Doses (nM): 0, 50, 100; Treatment period (hr): 24, +24 after removing CIDEC (post CIDEC); Drugs: Doxorubicin (DOX) @ 300 nm; Vemurafenib (VEM) @ 50 nm.
Figure 8B:
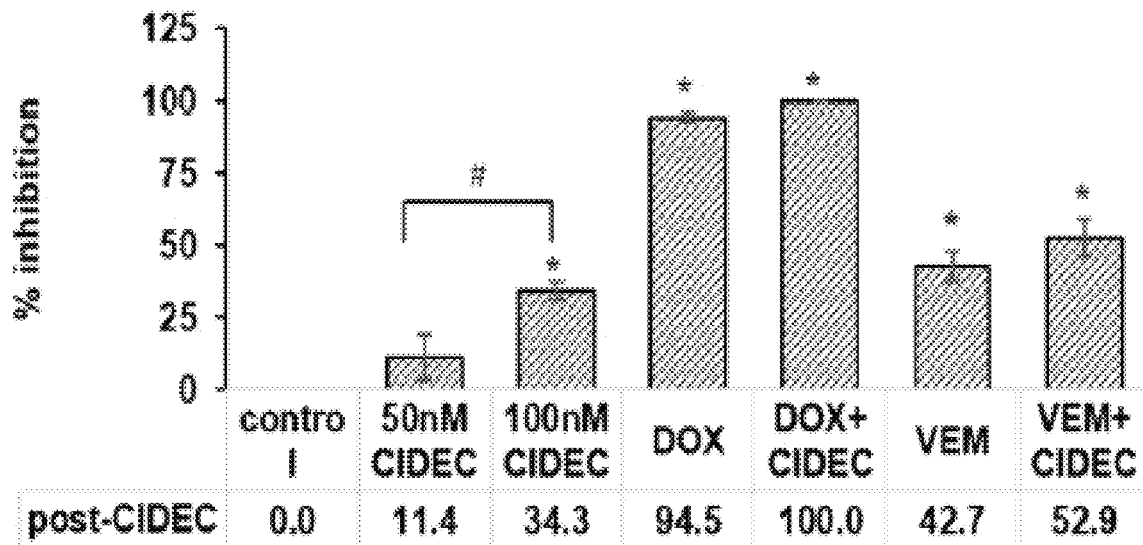

FIGS. 8A-8B show co-administration and 24 hr treatment with full-length CIDEC (fl-CIDEC) did not improve the cell inhibition rate of human melanoma cells above that of doxorubicin or vemurafenib.

Example 3—Anti-cancer Effect of Exogenously Added CIDEC Fragment Peptides

To confirm the residues in human full-length CIDEC protein critical for the anti-cancer effects, we designed six peptides of varying length (See FIG. 15— Table 1 for details). Human melanoma (SK-MEL-28) or liver cancer (HepG2) cells were treated with 50 or 100 nM fl-CIDEC or the fragment peptides for 48 hr. The fragments had variable effects on cancer cell viability, with fragment #3 showing maximum inhibition, followed by fragments #2 and #4.

Figure 9:
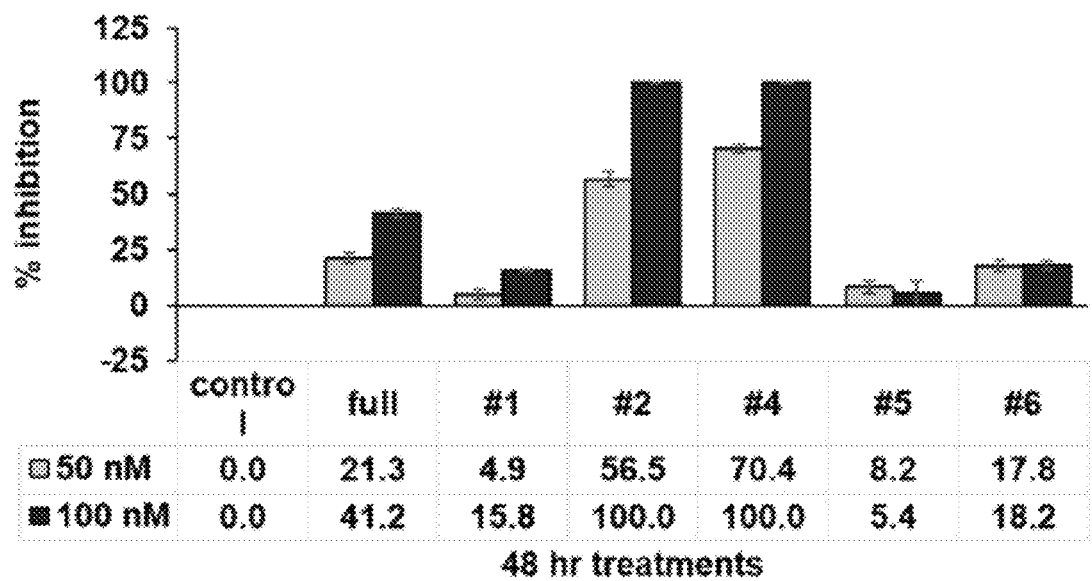
FIG. 9: Effect of CIDEC and fragment peptides on human liver cancer cell (HepG2) viability. [full-length CIDEC, #1, #2, #4, #5, #6=shorter fragment peptides of full-length CIDEC]; Cell: human liver cancer cells HepG2; Assay: Cell viability assay (Presto-Blue, Invitrogen); Doses (nM): 0, 50, 100; Treatment period (hr): 48.
Figure 10:
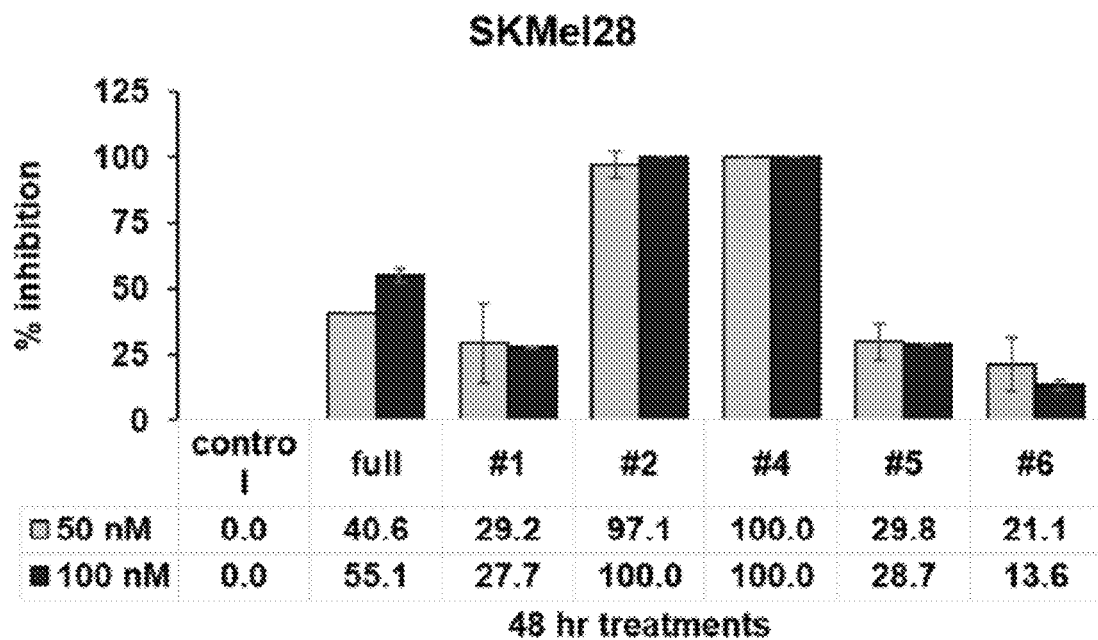
FIG. 10: Effect of CIDEC and fragment peptides on human melanoma cell (SK-MEL-28) viability. [full-length CIDEC, #1, #2, #4, #5, #6=shorter fragment peptides of full-length CIDEC]; Cell: human melanoma cells SK-MEL-28; Assay: Cell viability assay (Presto-Blue, Invitrogen); Doses (nM): 0, 50, 100; Treatment period (hr): 48.
Figure 11:
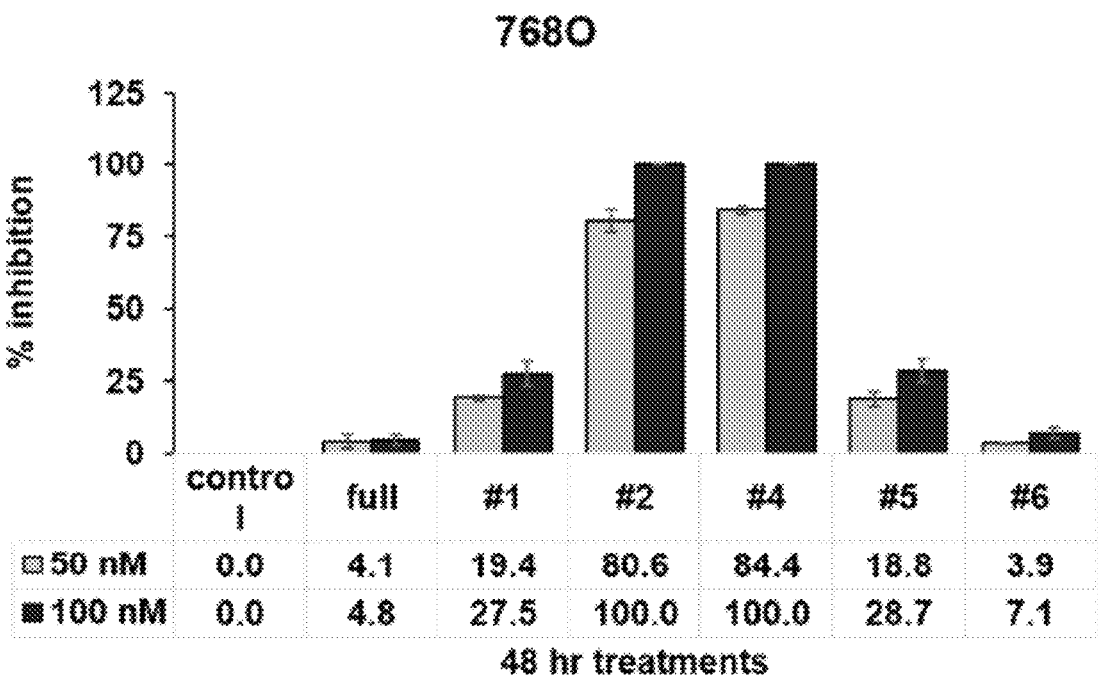
FIG. 11: Effect of CIDEC and fragment peptides on human renal cancer cell (786-0) viability. [full-length CIDEC, #1, #2, #4, #5, #6=shorter fragment peptides of full-length CIDEC]; Cell: human renal cancer cells; Assay: Cell viability assay (Presto-Blue, Invitrogen); Doses (nM): 0, 50, 100; Treatment period (hr): 48.

FIGS. 9, 10 and 11 show CIDEC fragment number 2 and 4 (SEQ ID NOs: 2 and 4, respectively) was found to be highly efficacious in inhibiting cell viability of human cancers of liver, kidney and melanoma at 50 nM concentrations. Cf1, Cf5 and Cf6 showed lower activity than the fl-CIDEC.

FIG. 9 shows Cf4 and Cf2 were found to completely (100%) inhibit cell viability of cancers of human liver (HepG2) at 100 nM in 48 hr.

FIG. 10 shows Cf4 and Cf2 were found to completely (100%) inhibit cell viability of cancers of melanoma (SK-MEL-28) at 100 nM in 48 hr.

FIG. 11 shows Cf4 and Cf2 were found to completely (100%) inhibit cell viability of cancers of kidney (786-0) at 100 nM in 48 hr.

Figure 12A:
FIG. 12A: Schematic illustration of FSP27 fragments/mutants: FSP27 (120-239); FSP27 (120-220); FSP27 (120-210); and, FSP27 (140-210).
Figure 12A:
Figure 12A:
Figure 12A:

FIG. 12A: Schematic illustration of FSP27 fragments/mutants: FSP27 (120-239); FSP27 (120-220); FSP27 (120-210); and, FSP27 (140-210).

Figure 12B:
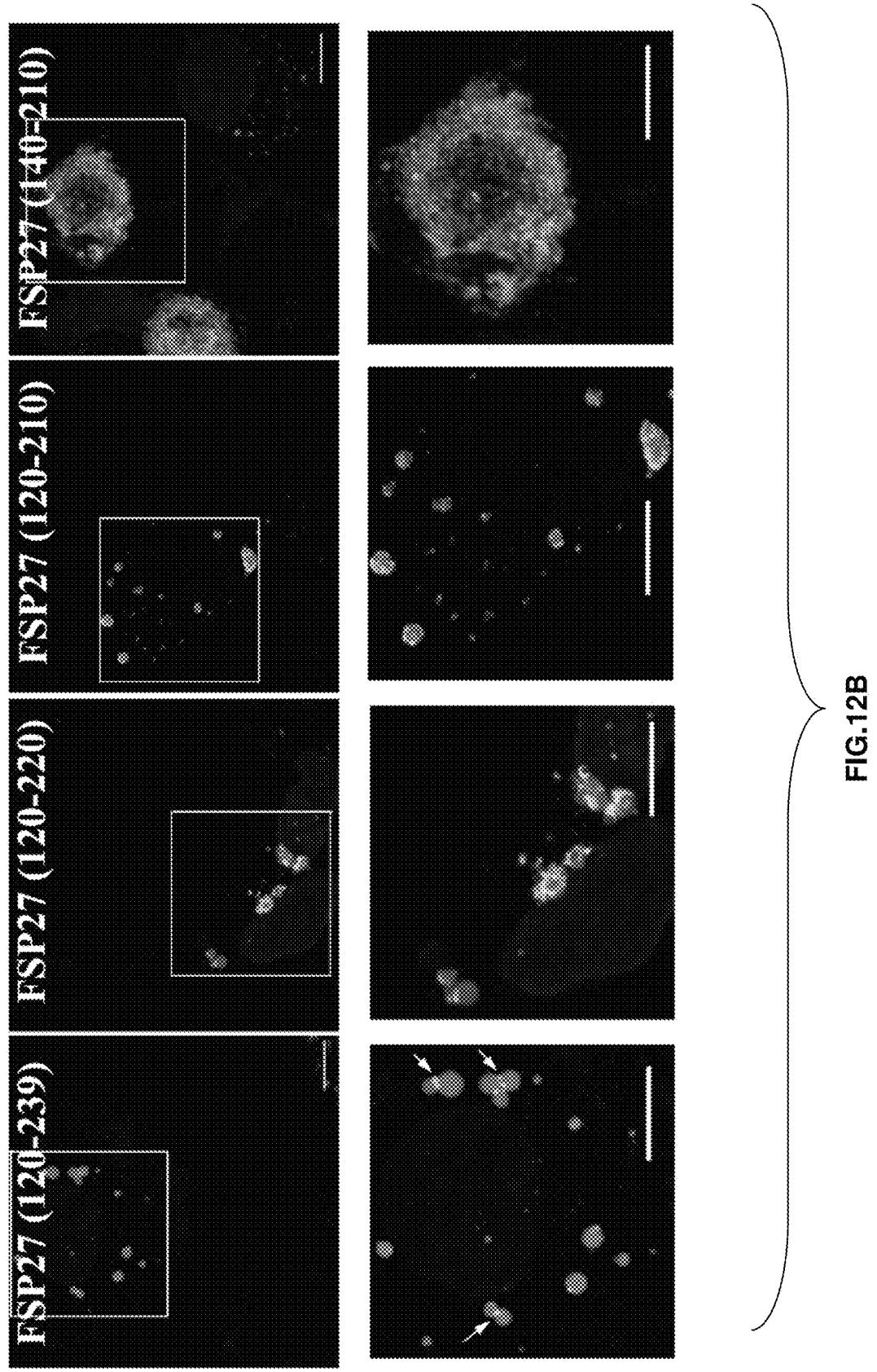
FIG. 12B: Expression of GFP fusion constructs of these deletions in COS7 cells; the images show the distribution of mutants (green) after 16 hr of transfection; Cells were labeled with Nile red (red), and nucleus was labeled with DAPI (blue).

FIG. 12B: Expression of GFP fusion constructs of these deletions in COS7 cells; the images show the distribution of mutants (green) after 16 hr of transfection; Cells were labeled with Nile red (red), and nucleus was labeled with DAPI (blue).

Figure 13:
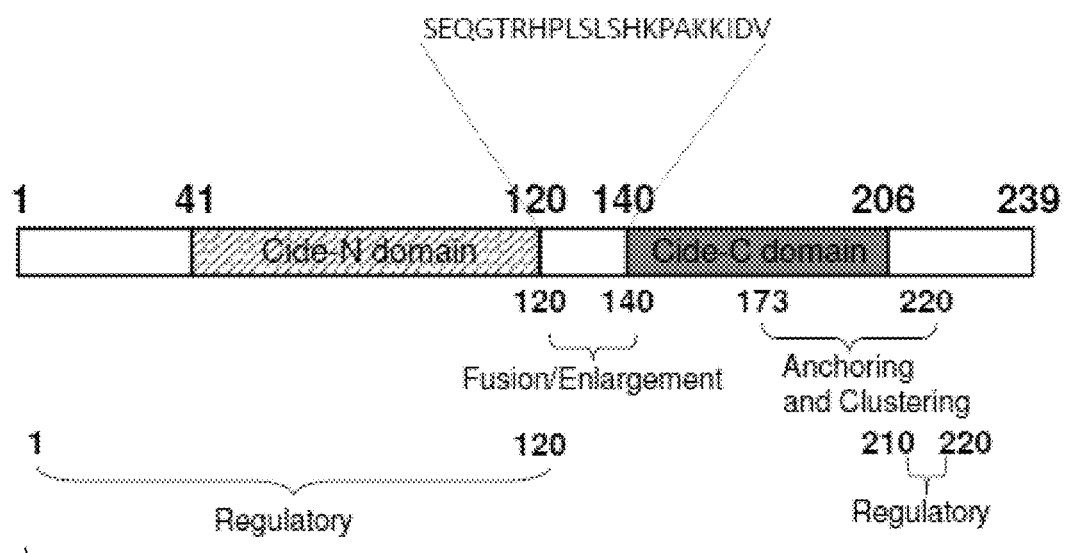
FIG. 13: Schematic illustration of full length FSP27 showing domains associated with lipid droplet dynamics.

FIG. 13: Schematic illustration of full length FSP27 showing domains associated with lipid droplet dynamics, and the segment 120-140 that has shown maximum efficacy towards anti-cancer effect in cells.

Figure 14:
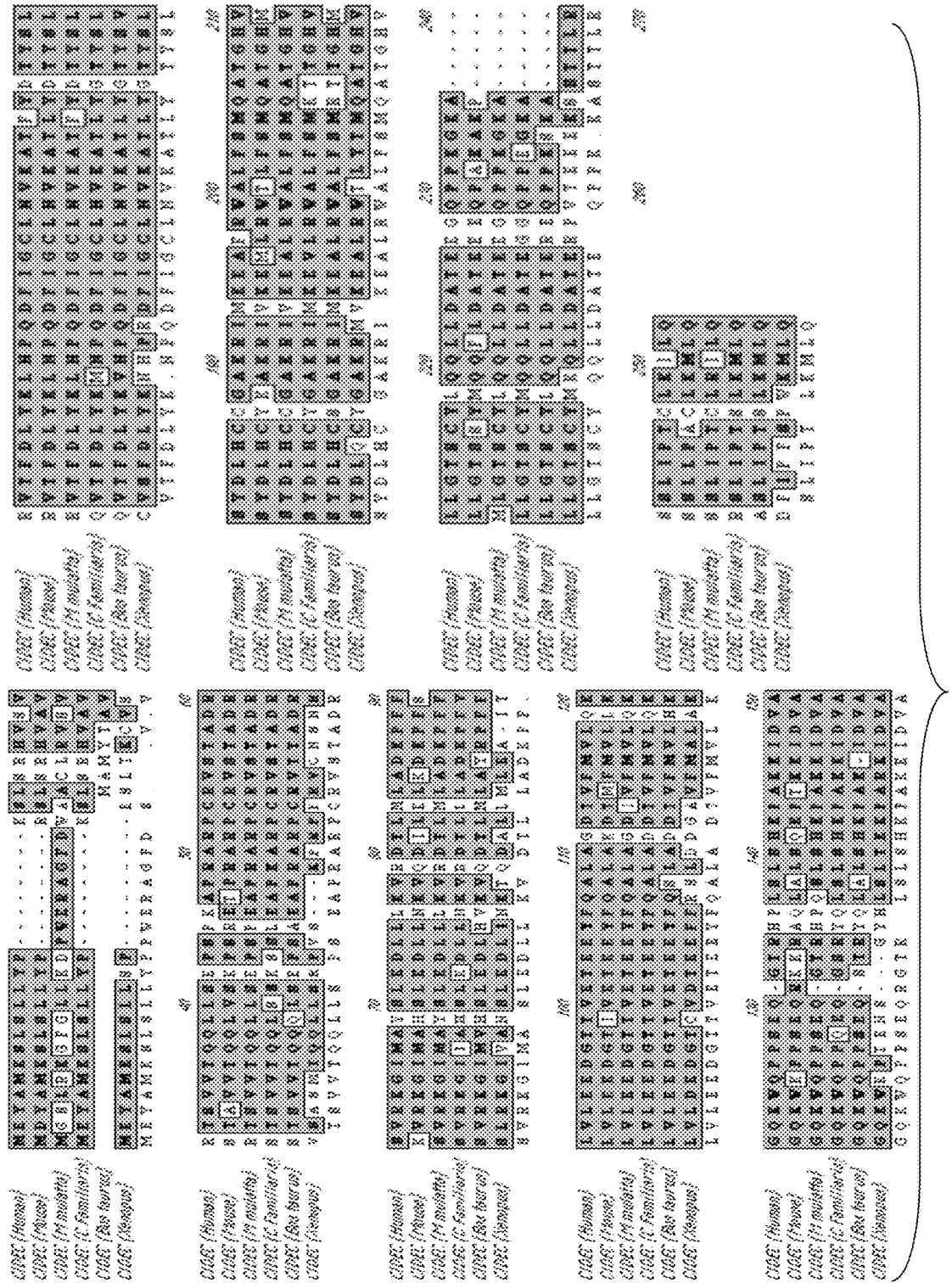
FIG. 14: FSP27 sequence is conserved in vertebrates; for example, >90% conserved sequence in FSP27 in humans (SEQ ID NO: 12), mouse (SEQ ID NO: 13), monkey (SEQ ID NO: 14), dog (SEQ ID NO: 15), cow (SEQ ID NO: 16) and frog (SEQ ID NO: 17).

FIG. 14 shows that the FSP27 sequence is conserved in vertebrates; for example, >90% conserved sequence in FSP27 in humans, mouse, monkey, dog, cow and frog.

FIG. 15: Table 1, shows the amino acid sequence detail of the relevant peptides tested for anti-cancer activity in cells.

Other Examples

Pharmaceutical Compositions

A pharmaceutical composition as described herein may be formulated with any pharmaceutically acceptable excipients, diluents, or carriers. A composition disclosed herein may comprise different types of carriers depending on whether it is to be administered in solid, liquid, or aerosol form, and whether it needs to be sterile for such routes of administration as injection. Compositions disclosed herein can be administered in a suitable manner, including, but not limited to topically (i.e., transdermal), subcutaneously, by localized perfusion bathing target cells directly, via a lavage, in creams, in lipid compositions (e.g., liposomes), formulated as elixirs or solutions for convenient topical administration, formulated as sustained release dosage forms, or by other method or any combination of the forgoing as would be known to one of ordinary skill in the art (see, for example, Remington's Pharmaceutical Sciences, 2003, incorporated herein by reference).

The compositions provided herein are useful for treating animals, such as humans. A method of treating a human patient according to the present disclosure includes the administration of a composition, as described herein.

The phrases "pharmaceutical" or "pharmacologically acceptable" refer to molecular entities and compositions that produce no adverse, allergic, or other untoward reaction when administered to an animal, such as, for example, a human. A carrier or diluent may be a solid, semi-solid, or liquid material which serves as a vehicle, excipient, or medium for the active therapeutic substance. Some examples of the diluents or carriers which may be employed in the pharmaceutical compositions of the present disclosure are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of *theobroma, arachis* oil, alginates, tragacanth, gelatin, syrup, methyl cellulose, polyoxyethylene sorbitan monolaurate, ethyl lactate, methyl and propyl hydroxybenzoate, sorbitan trioleate, sorbitan sesquioleate and oleyl alcohol, and propellants such as trichloromonofluormethane, dichlorodifluoromethane, and dichlorotetrafluoroethane.

The phrase "chemotherapeutic agent" refers to a therapeutic agent known to be used in treating a subject that has been diagnosed with cancer. Some examples of general classes of chemotherapeutic agents of the present disclosure include alkylating agents, anthracyclines, cytoskeletal disruptors, epothilones, histone deacetylase inhibitors, inhibitors of topoisomerase I and II, kinase inhibitors, nucleotide analogs and precursor analogs, peptide antibiotics, platinum-based agents, retinoids, and vina alkaloids and derivatives. Of these general classes, specific examples include but are not limite to doxorubicin (Adriamycin), sorafenib tosylate, cisplatin, paclitaxel, gemcitabine, vemurafenib, dabrafenib, linsitinib, crizotinib, and cabozantinib.

Solutions of the compositions disclosed herein as free bases or pharmacologically acceptable salts may be prepared in water suitably mixed with a surfactant, such as hydroxypropylcellulose. Dispersions may also be prepared in glycerol, liquid polyethylene glycols, and mixtures thereof, and in oils. Under ordinary conditions of storage and use, these preparations contain a preservative to prevent the growth of microorganisms. The pharmaceutical forms suitable for use include sterile aqueous solutions or dispersions and sterile powders for the extemporaneous preparation of sterile solutions or dispersions. In certain cases, the form should be sterile and should be fluid to the extent that easy injectability exists. It should be stable under the conditions of manufacture and storage and may optionally be preserved against the contaminating action of microorganisms, such as bacteria and fungi. The carrier can be a solvent or dispersion medium containing, for example, water, ethanol, a polyol (i.e., glycerol, propylene glycol, and liquid polyethylene glycol, and the like), suitable mixtures thereof, and/or vegetable oils. The prevention of the action of microorganisms can be brought about by various antibacterial and antifungal agents, for example, parabens, chlorobutanol, phenol, sorbic acid, thimerosal, and the like. In many cases, it may be preferable to include isotonic agents, such as, but not limited to, sugars or sodium chloride.

Pharmaceutical compositions for topical administration may include the compositions formulated for a medicated application such as an ointment, paste, cream, or powder. Ointments include all oleaginous, adsorption, emulsion, and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream, and petrolatum as well as any other suitable absorption, emulsion, or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed time-period.

It is further envisioned the compositions disclosed herein may be delivered via an aerosol. The term aerosol refers to a colloidal system of finely divided solid or liquid particles dispersed in a liquefied or pressurized gas propellant. The typical aerosol comprises a suspension of active ingredients in liquid propellant or a mixture of liquid propellant and a suitable solvent. Suitable propellants include hydrocarbons and hydrocarbon ethers. Suitable containers can vary according to the pressure requirements of the propellant. Administration of the aerosol can vary according to subject's age, weight, and the severity and response of the symptoms.

Dosage

The actual dosage amount of a composition disclosed herein administered to an animal or human patient can be determined by physical and physiological factors such as body weight, severity of condition, the type of disease being treated, previous or concurrent therapeutic interventions, idiopathy of the patient, and the route of administration. Depending upon the dosage and the route of administration, the number of administrations of a preferred dosage and/or an effective amount may vary according to the response of the subject. The compounds of the present disclosure are generally effective over a wide dosage range. The practitioner responsible for administration can, in any event, determine the concentration of active ingredient(s) in a composition and appropriate dose(s) for the individual subject.

Naturally, the amount of active compound(s) in each therapeutically useful composition may be prepared in such a way that a suitable dosage can be obtained in any given unit dose of the compound. Factors such as solubility, bioavailability, biological half-life, route of administration, product shelf life, as well as other pharmacological considerations can be contemplated by those preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. The dosages can depend on many factors, and can in any event be determined by a suitable practitioner. Therefore, the dosages described herein are not intended to be limiting In some embodiments, the compositions further include an additional active ingredient. The preparation of a pharmaceutical composition that contains at least one compound or additional active ingredient can be known to those of skill in the art in light of the present disclosure, as exemplified by Remington's Pharmaceutical Sciences, 2003, incorporated herein by reference. Moreover, for animal (e.g., human) administration, it can be understood that preparations should meet sterility, pyrogenicity, and general safety and purity standards as required by the FDA Office of Biological Standards.

Packaging of the Composition

After formulation, the composition is packaged in a manner suitable for delivery and use by an end user. In one embodiment, the composition is placed into an appropriate dispenser and shipped to the end user. Examples of final container may include a pump bottle, squeeze bottle, jar, tube, capsule or vial.

The compositions and methods described herein can be embodied as parts of a kit or kits. A non-limiting example of such a kit comprises the ingredients for preparing a composition, where the containers may or may not be present in a combined configuration. In certain embodiments, the kits further comprise a means for administering the composition, such as a topical applicator, or a syringe. The kits may further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive, CD-ROM, or diskette. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

What is claimed is:

1. A method for inhibiting cancer cell viability in a subject, comprising,
   contacting the cancer cell with a fat specific protein (FSP27) fragment or a pharmaceutically acceptable composition thereof, in an amount to decrease the cancer cell's viability;
   wherein the FSP27 fragment is Cf7 (SEQ ID NO: 7); and,
   wherein the cancer is pancreatic cancer.

2. The method of claim 1, wherein the cancer cell is a human cell.

3. The method of claim 1, wherein the composition is administered to the subject parenterally.

\* \* \* \* \*

```
SEQUENCE LISTING

Sequence total quantity: 17
SEQ ID NO: 1            moltype = AA  length = 60
FEATURE                 Location/Qualifiers
source                  1..60
                        mol_type = protein
                        organism = synthetic construct
                        note = Description of Artificial Sequence: Synthetic
                         polypeptide
SEQUENCE: 1
MEYAMKSLSL LYPKSLSRHV SVRTSVVTQQ LLSEPSPKAP RARPCRVSTA DRSVRKGIMA  60

SEQ ID NO: 2            moltype = AA  length = 48
FEATURE                 Location/Qualifiers
source                  1..48
                        mol_type = protein
                        organism = synthetic construct
                        note = Description of Artificial Sequence: Synthetic
                         polypeptide
SEQUENCE: 2
YDLHCCGAKR IMKEAFRWAL FSMQATGHVL LGTSCYLQQL LDATEEGQ                48

SEQ ID NO: 3            moltype = AA  length = 81
FEATURE                 Location/Qualifiers
source                  1..81
                        mol_type = protein
                        organism = synthetic construct
                        note = Description of Artificial Sequence: Synthetic
                         polypeptide
SEQUENCE: 3
PRARPCRVST ADRSVRKGIM AYSLEDLLLK VRDTLMLADK PFFLVLEEDG TTVETEEYFQ  60
ALAGDTVFMV LQKGQKWQPP S                                            81

SEQ ID NO: 4            moltype = AA  length = 21
FEATURE                 Location/Qualifiers
source                  1..21
                        mol_type = protein
                        organism = synthetic construct
                        note = Description of Artificial Sequence: Synthetic peptide
SEQUENCE: 4
SEQGTRHPLS LSHKPAKKID V                                            21

SEQ ID NO: 5            moltype = AA  length = 11
FEATURE                 Location/Qualifiers
source                  1..11
                        mol_type = protein
                        organism = synthetic construct
                        note = Description of Artificial Sequence: Synthetic peptide
SEQUENCE: 5
QQLLDATEEG Q                                                       11

SEQ ID NO: 6            moltype = AA  length = 29
FEATURE                 Location/Qualifiers
source                  1..29
                        mol_type = protein
                        organism = synthetic construct
                        note = Description of Artificial Sequence: Synthetic peptide
SEQUENCE: 6
QQLLDATEEG QPPKGKASSL IPTCLKILQ                                    29
```

```
SEQ ID NO: 7              moltype = AA   length = 119
FEATURE                   Location/Qualifiers
source                    1..119
                          mol_type = protein
                          organism = synthetic construct
                          note = Description of Artificial Sequence: Synthetic
                            polypeptide
SEQUENCE: 7
SEQGTRHPLS LSHKPAKKID VARVTFDLYK LNPQDFIGCL NVKATFYDTY SLSYDLHCCG   60
AKRIMKEAFR WALFSMQATG HVLLGTSCYL QQLLDATEEG QPPKGKASSL IPTCLKILQ   119

SEQ ID NO: 8              moltype = AA   length = 11
FEATURE                   Location/Qualifiers
source                    1..11
                          mol_type = protein
                          organism = synthetic construct
                          note = Description of Artificial Sequence: Synthetic peptide
SEQUENCE: 8
SEQGTRHPLS L                                                        11

SEQ ID NO: 9              moltype = AA   length = 91
FEATURE                   Location/Qualifiers
source                    1..91
                          mol_type = protein
                          organism = synthetic construct
                          note = Description of Artificial Sequence: Synthetic
                            polypeptide
SEQUENCE: 9
SEQGTRHPLS LSHKPAKKID VARVTFDLYK LNPQDFIGCL NVKATFYDTY SLSYDLHCCG   60
AKRIMKEAFR WALFSMQATG HVLLGTSCYL Q                                  91

SEQ ID NO: 10             moltype = AA   length = 101
FEATURE                   Location/Qualifiers
source                    1..101
                          mol_type = protein
                          organism = synthetic construct
                          note = Description of Artificial Sequence: Synthetic
                            polypeptide
SEQUENCE: 10
SEQGTRHPLS LSHKPAKKID VARVTFDLYK LNPQDFIGCL NVKATFYDTY SLSYDLHCCG   60
AKRIMKEAFR WALFSMQATG HVLLGTSCYL QQLLDATEEG Q                      101

SEQ ID NO: 11             moltype = AA   length = 71
FEATURE                   Location/Qualifiers
source                    1..71
                          mol_type = protein
                          organism = synthetic construct
                          note = Description of Artificial Sequence: Synthetic
                            polypeptide
SEQUENCE: 11
VARVTFDLYK LNPQDFIGCL NVKATFYDTY SLSYDLHCCG AKRIMKEAFR WALFSMQATG   60
HVLLGTSCYL Q                                                        71

SEQ ID NO: 12             moltype = AA   length = 238
FEATURE                   Location/Qualifiers
source                    1..238
                          mol_type = protein
                          organism = Homo sapiens
SEQUENCE: 12
MEYAMKSLSL LYPKSLSRHV SVRTSVVTQQ LLSEPSPKAP RARPCRVSTA DRSVRKGIMA   60
YSLEDLLLKV RDTLMLADKP FFLVLEEDGT TVETEEYFQA LAGDTVFMVL QKGQKWQPPS  120
EQGTRHPLSL SHKPAKKIDV ARVTFDLYKL NPQDFIGCLN VKATFYDTYS LSYDLHCCGA  180
KRIMKEAFRW ALFSMQATGH VLLGTSCYLQ QLLDATEEGP PKGKASSLIP TCLKILQ     238

SEQ ID NO: 13             moltype = AA   length = 239
FEATURE                   Location/Qualifiers
source                    1..239
                          mol_type = protein
                          organism = Mus sp.
SEQUENCE: 13
MDYAMKSLSL LYPRSLSRHV AVSTAVVTQQ LVSKPSRETP RARPCRVSTA DRKVRKGIMA   60
HSLEDLLNKV QDILKLKDKP FSLVLEEDGT IVETEEYFQA LAKDTMFMVL LKGQKWKPPS  120
EQRKKRAQLA LSQKPTKKID VARVTFDLYK LNPQDFIGCL NVKATLYDTY SLSYDLHCYK  180
AKRIVKEMLR WTLFSMQATG HMLLGTSSYM QQFLDATEEE QPAKAKPSSL LPACLKMLQ   239
```

```
SEQ ID NO: 14            moltype = AA  length = 246
FEATURE                  Location/Qualifiers
source                   1..246
                         mol_type = protein
                         organism = Macaca mulatta
SEQUENCE: 14
MGSLRKGFGL LKDPWERAGF DWAACLRVSV RTSVVTQQLL SEPSPEAPRA RPCRVSTADR   60
SVRKGIMAYS LEDLLLKVRD TLMLADKPFF LVLEEDGTTV ETEEYFQALA GDIVFMVLQK  120
GQKWQPPSEQ GTRHPQSLSH KPAKKIDVAR VTFDLYKLNP QDFIGCLNVK ATFYDTYSLS  180
YDLHCCGAKR IVKEALRWAL FSMQATGHVM LGTSCYLQQL LDATEEGQPP KGKASSLIPT  240
CLRILQ                                                             246

SEQ ID NO: 15            moltype = AA  length = 238
FEATURE                  Location/Qualifiers
source                   1..238
                         mol_type = protein
                         organism = Canis familiaris
SEQUENCE: 15
MEYAMKSLSL LYPKSLSRHV AVSTSVVTQQ LSSKSSLEAP KARPCRVSTA DRSVRKGIIA   60
HSLKDLLNKV RDTLLLADKP FYLVLEEDGT TVETEEYFQA LADDTVFMVL QKGQKWQPPQ  120
EQGSRYQLSL SHKPAKKIDV AQVTFDLYKM NPQDFIGCLN VKATLYGTYS LSYDLHCYGA  180
KRIMKEVLRW ALFSMKTTGH VLLGTSCYMQ QLLDATEGGQ PPEGKARSLI PTSLKMLQ    238

SEQ ID NO: 16            moltype = AA  length = 222
FEATURE                  Location/Qualifiers
source                   1..222
                         mol_type = protein
                         organism = Bos taurus
SEQUENCE: 16
MAMYTAVSTS VVTQQQLSEP SAEAPRARPC RVTTADRSVR KGIMVHSLED LHVKVQDTLM   60
LAYRPFFLVL EEDGTTVETE EYFQSLADDT VFMVLHKGQK WQPPSEQSTR YQLALSHKPA  120
KIDVAQVTFD LYKVNPQDFI GCLNVKATLY GTYSVSYDLH CSGAKRIMKE ALRWALFSMR  180
TTGHMLLGTS CYLQQLLDAT EREQPPKSKA ASLIPTSLKM LQ                     222

SEQ ID NO: 17            moltype = AA  length = 236
FEATURE                  Location/Qualifiers
source                   1..236
                         mol_type = protein
                         organism = Xenopus sp.
SEQUENCE: 17
MEYAMKSLSL LSPKSLTKCV SVSASMTQQL LSRPVSKPRP FRVCNSNRSL RKGIVANSLE   60
DLINKTQDAL LMLEAITLVL DEDGTCVDTE EFFRSLDDGA VFMALAKGQK WKPTENSGYH  120
LSLTKKPARK IDVACVSFDL YKNHPRDFIG CLNVKATLYG TYSLSYDLQC YGAKRMVKEA  180
LRWTLYTMQA TGHVLLGTSC YMKQLLDATE RPVTEEEKSS TTLRDFIPFS PWKMLQ      236
```